US009744329B2

(12) United States Patent
Billingsley et al.

(10) Patent No.: US 9,744,329 B2
(45) Date of Patent: *Aug. 29, 2017

(54) AIR FILTRATION DEVICE HAVING SUBSECTIONS LACKING FLUID COMMUNICATION

(71) Applicant: 3M INNOVATIVE PROPERTIES COMPANY, St. Paul, MN (US)

(72) Inventors: Britton G. Billingsley, St. Paul, MN (US); David M. Blomberg, Lino Lakes, MN (US); Joy L. Manske, Menomonie, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,372

(22) Filed: Nov. 3, 2014

(65) Prior Publication Data

US 2015/0047633 A1     Feb. 19, 2015

Related U.S. Application Data

(63) Continuation of application No. 13/326,451, filed on Dec. 15, 2011, now Pat. No. 8,899,227.

(51) Int. Cl.
*A61M 16/00* (2006.01)
*A61M 16/10* (2006.01)
(Continued)

(52) U.S. Cl.
CPC ...... *A61M 16/105* (2013.01); *A61M 16/0003* (2014.02); *A61M 16/0683* (2013.01);
(Continued)

(58) Field of Classification Search
CPC .......... A61M 16/0003; A61M 16/0683; A61M 16/105; A61M 2016/0027;
(Continued)

(56) References Cited

U.S. PATENT DOCUMENTS 3,621,841 A    11/1971    Austin
3,873,287 A     3/1975    Barnebey
(Continued)

FOREIGN PATENT DOCUMENTS

CN    101081328    12/2007
CN    201750974     2/2011
(Continued)

OTHER PUBLICATIONS

European Application No. 12858131 Search Report dated Oct. 12, 2015.

*Primary Examiner* — Bradley Philips

(57) ABSTRACT

A filtering device 10 that includes a housing 12 having a plurality of subsections 32, 34, and 36 where each subsection contains a filter element 26, 28, and 30. An inlet 18 is disposed at a first location on the housing 12, and an upstream air distribution system is placed in fluid communication with the inlet 18 and with each of the subsections 32, 34, and 36. A downstream air distribution system is located in fluid communication with each subsection 32, 34, and 36, and an outlet 20 is in fluid communication with the downstream air distribution system. The subsections are fashioned such that each subsection 32, 34, and 36 is not in fluid communication with each other. Using a filtering device so constructed, airflow through the device may be better managed to enable overall product service life to be increased while minimizing pressure resistance of the total filter.

20 Claims, 4 Drawing Sheets

(51) Int. Cl.
*A62B 7/10* (2006.01)
*A62B 18/04* (2006.01)
*A61M 16/06* (2006.01)
*B01D 29/00* (2006.01)
*B01D 46/12* (2006.01)

(52) U.S. Cl.
CPC .............. *A62B 7/10* (2013.01); *A62B 18/045* (2013.01); *A61M 2016/0027* (2013.01); *A61M 2205/3331* (2013.01); *A61M 2205/75* (2013.01); *B01D 29/0059* (2013.01); *B01D 46/12* (2013.01)

(58) Field of Classification Search
CPC ...... A61M 2205/3331; A61M 2205/75; A61M 16/1055; A61M 16/106; A61M 16/1065; A61M 16/1045; B01D 29/0059; B01D 29/56; B01D 46/0023; B01D 46/12; B01D 46/125; F24F 13/28; A62B 18/045; A62B 7/10; A62B 23/02
See application file for complete search history.

(56) References Cited

U.S. PATENT DOCUMENTS

| | | | |
|---|---|---|---|
| 3,971,373 A * | 7/1976 | Braun | A62B 23/025 128/206.19 |
| 4,186,736 A | 2/1980 | Angioletti | |
| 4,280,491 A | 7/1981 | Berg | |
| 4,462,399 A | 7/1984 | Braun | |
| 4,501,272 A | 2/1985 | Shigematsu | |
| 4,852,562 A | 8/1989 | Howie | |
| 4,858,627 A | 8/1989 | Netschert | |
| RE33,118 E | 11/1989 | Scheitlin | |
| 5,035,239 A | 7/1991 | Edwards | |
| 5,104,430 A | 4/1992 | Her-Mou | |
| 5,283,914 A | 2/1994 | James | |
| H1360 H | 10/1994 | Grove | |
| RE35,062 E | 10/1995 | Brostrom | |
| 5,533,500 A | 7/1996 | Her-Mou | |
| 5,577,495 A | 11/1996 | Murphy | |
| 5,660,173 A | 8/1997 | Newton | |
| 5,732,695 A | 3/1998 | Metzger | |
| 5,964,221 A | 10/1999 | McKenna | |
| 5,992,414 A | 11/1999 | Tayebi | |
| 6,014,971 A | 1/2000 | Danisch | |
| 6,055,983 A | 5/2000 | Metzger | |
| 6,176,239 B1 | 1/2001 | Grove | |
| 6,233,748 B1 | 5/2001 | Geiger | |
| 6,279,570 B1 | 8/2001 | Mittelstadt | |
| 6,298,849 B1 | 10/2001 | Scholey | |
| 6,338,341 B1 | 1/2002 | Drews | |
| 6,345,620 B2 | 2/2002 | Salapow | |
| 6,367,085 B1 | 4/2002 | Berg | |
| 6,447,566 B1 | 9/2002 | Rivera | |
| 6,467,481 B1 | 10/2002 | Eswarappa | |
| 6,666,209 B2 | 12/2003 | Bennett | |
| 6,736,138 B2 | 5/2004 | Tayebi | |
| 6,793,702 B2 | 9/2004 | Eswarappa | |
| 6,796,304 B2 | 9/2004 | Odell | |
| 6,823,867 B2 | 11/2004 | Avery | |
| 6,826,783 B1 | 12/2004 | Grove | |
| 6,934,967 B2 | 8/2005 | Miyashita | |
| 6,954,944 B2 | 10/2005 | Feher | |
| 7,104,264 B2 | 9/2006 | Lee | |
| 7,197,774 B2 | 4/2007 | Curran | |
| 7,311,764 B2 | 12/2007 | Friday | |
| 7,637,622 B2 | 12/2009 | Magnusson | |
| 7,748,381 B2 | 7/2010 | Croll | |
| 7,810,492 B2 | 10/2010 | Church | |
| 7,861,719 B1 | 1/2011 | Grove | |
| 7,947,109 B2 | 5/2011 | Sayers | |
| 8,234,722 B2 | 8/2012 | VanDerWoude | |
| 8,292,991 B2 | 10/2012 | Friday | |
| 8,887,719 B2 | 11/2014 | Billingsley | |
| 8,899,227 B2 | 12/2014 | Billingsley | |
| 2003/0066121 A1 | 4/2003 | Diaz | |
| 2003/0089089 A1 | 5/2003 | Fecteau | |
| 2004/0040561 A1 | 3/2004 | Tayebi | |
| 2005/0169820 A1 | 8/2005 | Tatarchuk et al. | |
| 2005/0223902 A1 | 10/2005 | Lovell | |
| 2005/0241642 A1 | 11/2005 | Kryszoftik | |
| 2006/0048782 A1 | 3/2006 | Gossweiler | |
| 2006/0101557 A1 | 5/2006 | Klotz | |
| 2007/0283961 A1 * | 12/2007 | Hsieh | A62B 17/006 128/205.29 |
| 2008/0105255 A1 | 5/2008 | Resnick | |
| 2008/0289632 A1 | 11/2008 | Dankert | |
| 2011/0283505 A1 | 11/2011 | Billingsley | |
| 2013/0139818 A1 | 6/2013 | Billingsley | |

FOREIGN PATENT DOCUMENTS

| | | |
|---|---|---|
| DE | 10337652 | 3/2005 |
| GB | 2061696 | 5/1981 |
| KR | 20-2010-0003793 | 4/2010 |
| WO | WO 86/01430 | 3/1986 |
| WO | WO 2008/153455 | 12/2008 |
| WO | WO 2009/137770 | 11/2009 |
| WO | WO 2011/126884 | 10/2011 |

* cited by examiner

AIR FILTRATION DEVICE HAVING SUBSECTIONS LACKING FLUID COMMUNICATION

This invention was made with Government support under contract with the Department of Defense, Contract No. W911SR-09-C-0037. The Government has certain rights in this invention.

The present invention pertains to an air filtration device that has a plurality of subsections which each contain a filter element and which are not in fluid communication with each other.

BACKGROUND

Respirators that filter air for breathing are frequently worn by individuals who work in areas where contaminated air is present. The respirators may operate under negative pressure, in which the wearer's lungs provide the power that draws air through the filter (see, for example, U.S. Pat. RE35,062 to Brostrom et al.), or they may operate using positive pressure, in which a fan or other device drives the ambient air through the filter (see, for example U.S. Pat. No. 7,748,381 to Croll et al). A powered air purifying respirator (PAPR) is often desired by users because the wearer does not have to supply the energy needed to force the ambient air through the air filter. The wearer accordingly feels more comfort and may use the saved energy for other tasks.

PAPRs typically have (i) an electric motor and blower unit to force the air through the filter, (ii) a facepiece for delivering the clean air to the user, and (iii) a power source, such as a battery pack, to supply the energy needed to power the device. Known PAPRs have been assembled in a variety of configurations, but two common types are belt pack PAPRs and helmet PAPRs. Belt pack PAPRs typically have the filtering unit worn about the user's waist, whereas helmet PAPRs have the filtering unit contained within the helmet. In both systems, an electrically-powered fan drives or draws the air through the filter cartridges, through the hose, and into the facepiece interior. Because the fan does the work required for air movement through the PAPR system, the user is able to comfortably receive a clean supply of air with little effort.

Helmet-style PAPRs typically use a supported filter bag to filter air before it enters the interior gas space for breathing. The filter bag holders sometimes have only limited or no support through the center of the filter bag because the airflow alone is sufficient to keep the filter layers separated. FIG. 1 shows a filter support used in some helmet-mounted respirators. The filter bag holder 110 is designed to support a flat filter bag in an arcuate form to fit within the crown space of a helmet. The holder 110 is constructed of two members 112 and 114, with the smaller member 114 being held in compression to provide an opening 116 between the two members at one end thereof. Both members 112 and 114 include a plurality of openings 118 and 120, respectively, that are aligned along the length of the holder 110. The filter bag holder 110 is designed primarily to maintain the filter bag in an arcuate shape. An example of a helmet-mounted PAPRs system is disclosed in U.S. Pat. No. 4,280,491 to Berg et al.

Another product that maintains the filtering bag in an arcuate shape is disclosed in U.S. Pat. No. 6,279,570 to Mittelstadt et al. As shown in FIG. 2, this filter support 200 has ribs 210 and 220 that are generally aligned with the longitudinal axis of the device. Some of the support ribs 210 are laterally offset from adjacent ribs 220. FIG. 3 shows how the filtration bag 310 may be placed around the support 200 in a helmet 300.

Another PAPR is described in International Publication WO 2011/126884 to Ausen. In this device the blower is placed within the helmet along with the filter media and a plenum that delivers ambient air to the filter. Air that exits the filter media then passes into another plenum where it is pulled into a blower assembly located centrally within the helmet. After passing through the blower assembly, the filtered air is then delivered to the wearer via a filtered air outlet and a filtered air passageway.

Although these conventional filtering devices have provided good support for the filtering material and have demonstrated good filtration of the air that passes through the device, the devices have not allowed for the controlled flow of air through the filter media. Without such controlled flow, certain portions of the filter media may become expended before others, resulting in an earlier ending of the service life.

SUMMARY OF THE INVENTION

The present invention provides an air filtration device that comprises a housing that includes a plurality of subsections where each subsection contains a filter element. An inlet is disposed at a first location on the housing. An upstream air distribution system is in fluid communication with the inlet and with each of the subsections. A downstream air distribution system is located in fluid communication with each subsection, and an outlet is in fluid communication with the downstream air distribution system. The housing subsections are not in fluid communication with each other.

The present invention is beneficial in that air flow through the device may be better managed. When using a plurality of filtering subsections that are not in fluid communication with each other, the air management can be fashioned to enable each filter element to be exposed to similar airflow volumes, causing no filter element to reach the end of its service life substantially before the others. Overall service life of the device may therefore be increased. The pressure resistance of the total filter also may be minimized because the air flow may pass through all of the filter media equally, thereby increasing the amount of filter media being used—compared to a filter with air flow distribution issues where all air flow is pushed through a small portion of the available media.

Glossary

The terms set forth below will have the meanings as defined:

active particulate means particles or granules that are specially suited to perform some action or function such as sorption (adsorption and/or absorption), catalysis, and ion exchange;

air distribution system means a part or combination of parts which assist in controlling the air flow;

air flow means greater than insignificant or immeasurable air movement;

airflow velocity means a pressure exhibited by moving air relative to a baseline pressure;

baseline pressure means pressure measured at ambient pressure or at a location common to air flows to or from other locations where pressure is measured;

clean air means a volume of ambient air that has been filtered to remove contaminants;

contaminants means particles (including dusts, mists, and fumes) and/or other substances that generally may not be considered to be particles (e.g., organic vapors, et cetera) but which may be suspended in the ambient air;

crown space means the space between a wearer's head and the interior side of a helmet;

downstream means located at point in time in an air stream later than the reference point to which it refers;

exhaled air means air that is exhaled by a person;

filtering device means a device that is designed to remove contaminants from air;

filter media or filter element means an air permeable material that is designed to remove contaminants from air that passes through it;

fluid inlet means an area, surface, or volume of space through which air can enter;

filter layer means an air-permeable structure that includes one or more layers and that is designed to remove contaminants from air that passes through it;

fluid outlet means an area or portion through which air can exit;

HEPA class and High Efficiency Particulate Air class define the performance of filter material as set forth in 42 C.F.R. §84 (1995);

helmet means an apparatus that is adapted to be worn on the head of a person for purposes of protecting the head from impact;

housing means a structure or combination of parts that is fashioned for housing or containing another item wholly or partially;

interior gas space means the space in front of a person's face where clean air can be inhaled;

longitudinal axis means an axis that extends generally along the length of the filtering device;

manifold means a two or more channels or passageways that distribute air to or from a plenum;

not in fluid communication means that the same air does not pass through;

plenum means a common volume of space where air flows into from more than one location or from where air flows to more than one location;

powered air purifying respirator or PAPR means a device that is capable of supplying clean air to a wearer where the air is filtered on the wearer through use of energy from a source other than the wearer;

substantially the same means within 10% of another;

transverse axis means an axis that extends generally perpendicular to the longitudinal axis; and upstream means located at a point in time in an air stream before the reference point to which it refers.

DETAILED DESCRIPTION OF PREFERRED EMBODIMENTS

In the practice of the present invention, a filtering device is provided which includes a housing, an inlet, a first air distribution system, a second air distribution system, and an outlet. The housing includes a plurality of subsections where each subsection contains at least one filter element. The inlet is disposed at a first location on the housing. The first air distribution system is in fluid communication with the inlet and with each of the subsections. The second air distribution system is located in fluid communication with each subsection. The outlet is in fluid communication with the second air distribution system. The subsections are not in fluid communication with each other. This non-fluid communication may be accomplished by designing the plenum(s), manifold(s), and/or ports leading into the subsections to deliver the air to-be-filtered to each subsection in parallel. Using such a construction, the airflow velocity through each subsection may be substantially the same. The subsections therefore may filter similar amounts of ambient air, allowing no filter to meet the end of its service life substantially before the others.

Figure 1:
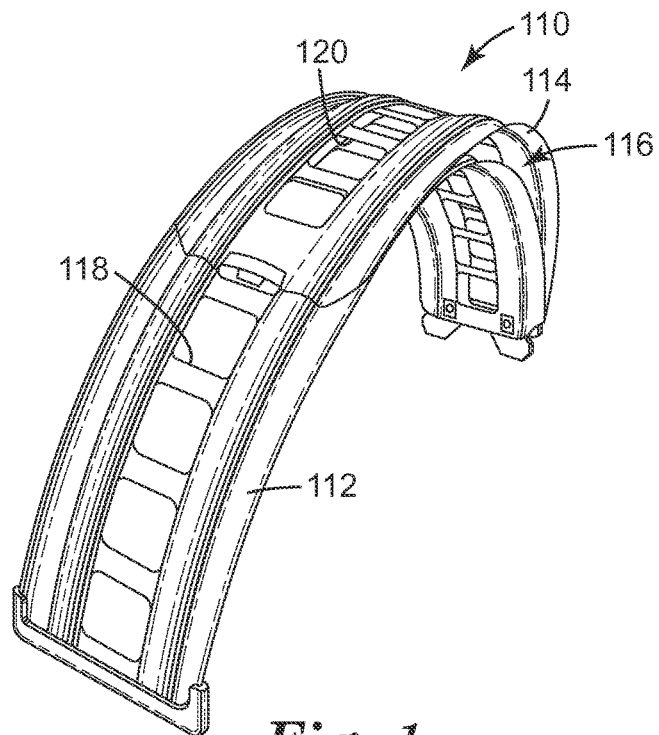
FIG. 1 is a perspective view of a prior art filter support 110 useful in a helmet-mounted respirator.
Figure 2:
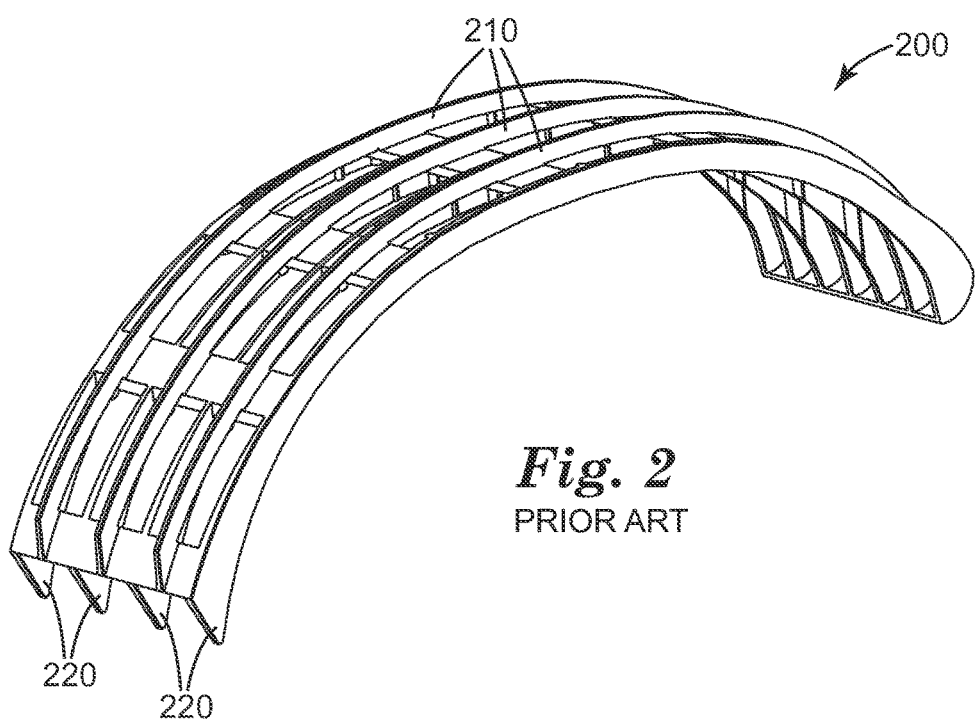
FIG. 2 is a perspective view of known device 200 for maintaining a known filtering bag in an arcuate shape.
Figure 3:
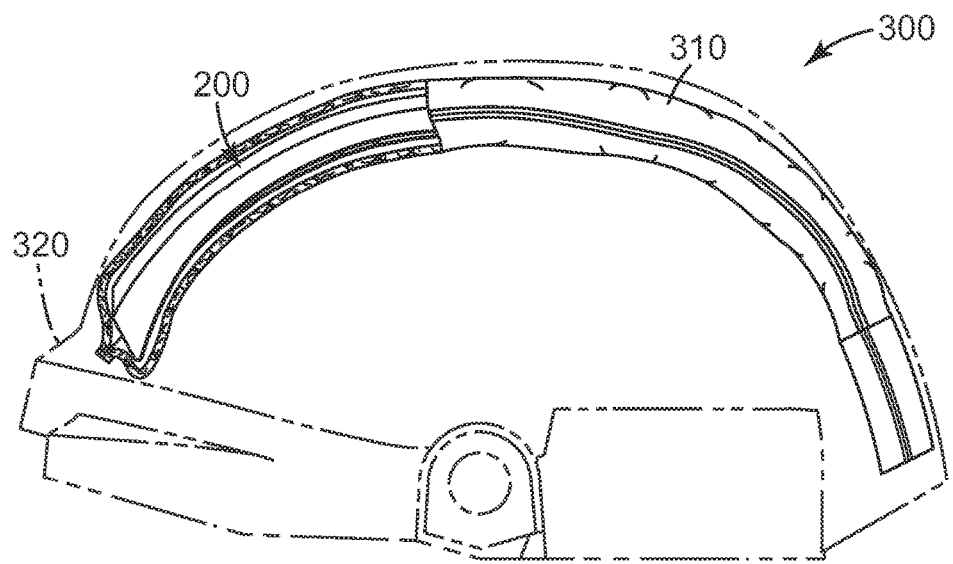
FIG. 3 is a side view of the prior art filtering device 200 placed within the confines of a helmet 300.
Figure 4:
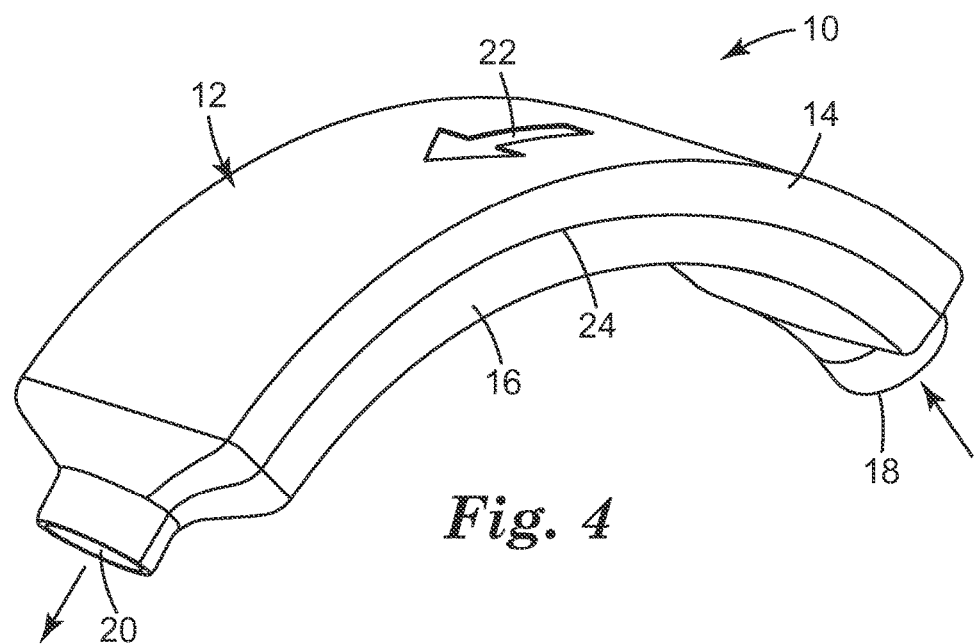
FIG. 4 is perspective view of a filtering device 10 in accordance with the present invention.

FIG. 4 shows a filtering device such as a filter cartridge 10 that can be used in a personal respiratory protection device to provide the user with clean air to breathe. The filtering device 10 includes a housing 12 that has an upper portion or half 14 and a lower portion of half 16. Air that is to be filtered enters the housing 12 at an inlet 18 and exits the device at an outlet 20. The air thus passes through the device in the direction of the arrow 22. The air that enters the device 10 at inlet 18 is unfiltered, whereas air that exits the device at outlet 20 is filtered—that is, it is clean air safe for a user of the device to breathe. As the air moves through the housing interior, the air passes through one or more filter elements where contaminants can be removed from the airstream. The housing 12 may be curved in the longitudinal dimension as shown, that is, around the transverse axis, so that the device may be used as a cartridge located in the crown space of a helmet. The housing 12 also could be curved perpendicular to the longitudinal dimension or along the longitudinal axis or dimension to further accommodate the crown space in a helmet. The first and second portions 14 and 16 of the housing 12 are joined together at a midline 24. The device may be separated along line 24 to replace the filter elements if so desired.

Figure 5:
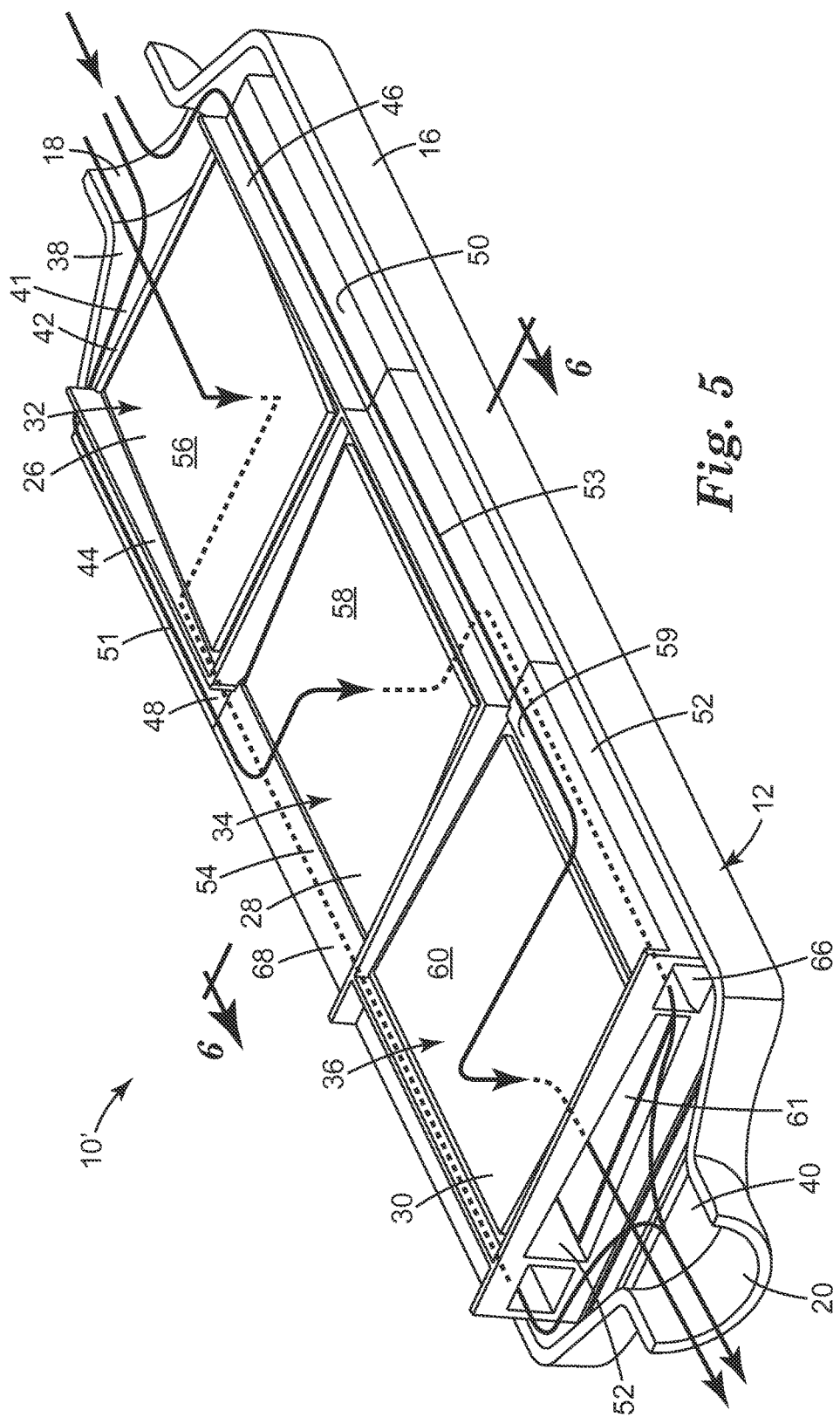
FIG. 5 is a perspective view of the filtering device 10' having the upper half 14 of the housing 12 being removed.
Figure 6:
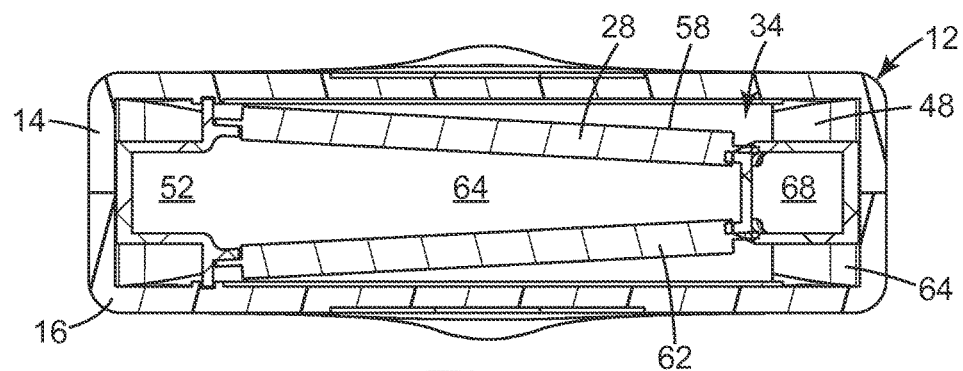
FIG. 6 is a cross section of the filtering device 10' taken along lines 6-6 of FIG. 5.

FIGS. 5-6 show the filtering device in a planar rather than a curved configuration. In these figures, the top portion 14 (FIG. 4) of the housing 12 is removed so that the housing interior may be seen, as well as the filter elements 26, 28, and 30 located in subsections 32, 34, and 36, respectively. The subsections 32, 34, and 36 provide a defined area for the filter Elements 26, 28, and 30 to reside within the housing 12. The subsections 32, 34, and 36 are not in fluid communication with each other. In addition to the housing 12, the filtering device 10' includes an inlet 18, a first plenum 38, a second plenum 40, and an outlet 20. The first Plenum 38 is in fluid communication with the inlet 18 and with each of the subsections 32, 34, And 36. The second plenum 40 also is located in fluid communication with each subsection 32, 34, and 36. The outlet 20 also is in fluid communication with the second plenum 40. The first and second plenum 38, 40 and the air manifolds that are associated with them are constructed to cause the same airflow velocity through each subsection 32, 34, and 36. Air that enters the first plenum 38 from the inlet 18 passes in one of three different directions toward one of the three subsections 32, 34, and 36. Air may travel to the first subsection 32 through the opening or port 41 in the subsection 32 at the first end 42. The opening in the subsection 32 is defined at the first end 42 by subsection sidewalls 44 and 46 and the top half 14 (FIG. 4) of the housing 12. Ambient air passing to the second and third filter elements 28 and 30 may do so through upper channels 48 and 50, respectively, as noted by air flow lines 51 and 53. Air that passes through the opening 41 at the first end 42 of first subsection 32 passes through the face 56 of the first filter element 26; air that passes through the opening 54 of the second subsection 34 passes through the face 58 of the second filter element 28; and air that passes through the opening 59 of the third subsection 36 passes through the face 60 of the third filter element 30. Air exiting the second and third subsections after being filtered passes through passageway 52 and opening 61 to enter plenum 40.

FIG. 6 shows, in particular, that each subsection may include first and second filter elements. Illustrated middle subsection 34, for example, includes opposing filter elements 28 and 62. Air arrives at filter element 62, through lower channel 64, in a manner similar to air arriving at filter element 28 through upper channel 48 as described above. Each filter element 28 and 62 is tilted relative to the air entering the subsection to enable the air to better pass through the filter media. Air that passes through filter elements 28 and 62 enters plenum 64 to then pass into passageway 52 where it then is directed out exit port 66 (FIG. 5) to enter plenum 40. Air in subsection 32 (FIG. 5) similarly passes through opposing filter elements to enter a central plenum where it then is subsequently directed into passageway 68. Split flow of the airstream may be carried out as described in U.S. Patent application entitled Split Flow Filtering Device (U.S. Ser. No. 13/310,881) to Billingsley et al. Although the filtering device of the present invention is shown with three subsections, the device may have 2, 3, 4, 5 to 10, 20 or more subsections. The airflow velocity through each subsection is substantially the same, preferably within about 5% of each other.

Figure 7:
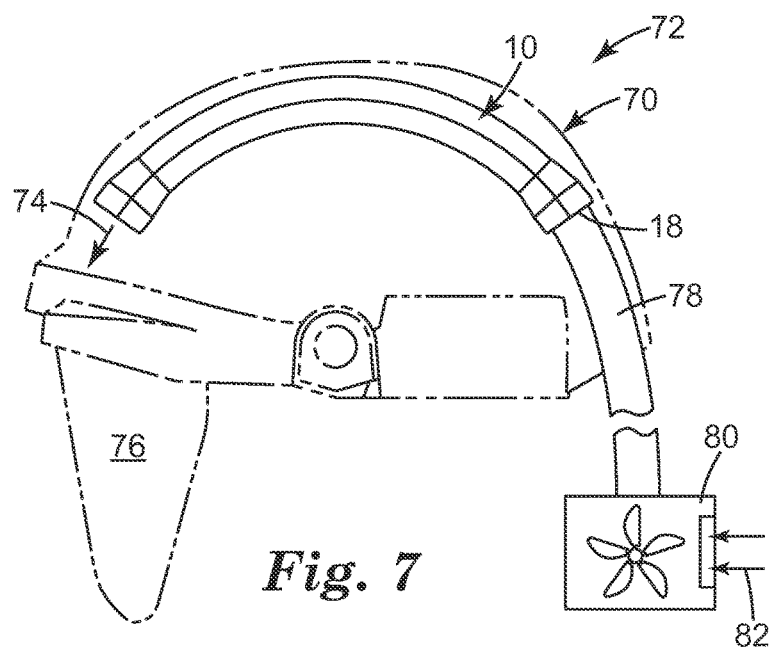
FIG. 7 is a side view of the filtering device 10 positioned in a helmet 70.

FIG. 7 shows an example of a curved filtering device 10 in accordance with the present invention being used in the crown space of a helmet 70 of a PAPR 72. Clean air 74 that exits the filtering device 10 enters the interior gas space 76 of the helmet 70 where it can he inhaled by the wearer. Atmospheric air is supplied to the fluid inlet 18 of the device 10 via a conduit 78. A blower 80 drives or forces the unfiltered air 82 through the conduit 78 into the inventive filtering device 10. The blower 80 can be operatively powered by a suitable power source such as a battery, which may exhibit passivation—see U.S. Pat. No. 7,947,109 to Sayers et al. The blower 80 can be positioned on a belt worn by the user, and it also can be positioned to be isolated from the exterior environment—see U.S. Pat. No. 6,796,304 to Odell et al.; see also U.S. Pat. No. 6,823,867 to Avery et al. The air flow also can be calibrated in the respirator system—see U.S. Pat. No. 6,666,209 to Bennett et al. and managed otherwise—see U.S. Pat. No. 7,197,774 to Curran et al. A flow indicator may be used to alert the wearer if air flow falls below a predetermined value. Because air passes through a plurality of subsections, more surface area is available for filtering, thereby lowering the pressure drop across the device 10. Lower pressure drop means that less energy is needed to drive the ambient air through the filter media. Further the additional surface area may extend the service life of the media since it may take longer for the pores in the media to become plugged with various contaminants. The helmet could be, for example, a welding helmet—see, for example, U.S. Pat. No. 6,934,967 to Miyashita et al. and U.S. Pat. No. 7,637,622 to Magnusson et al.—with a head suspension system (U.S. Pat. No. 6,367,085 to Berg. The invention also could be used in a hooded device—see U.S. Pat. No. 7,104,264 to Lee et al.

The plenums and manifolds of the air distribution systems may be defined by the shape and configuration of the housing and the first, second, third, and other subsections. The plenum may include physical structure that assists in providing structure to the overall device and the manifolds may include the physical structure that is used to define the channels and passageways that assist in splitting fluid flow into two or more flow streams towards two or more independently operating filter media containing subsections.

The housing may be fashioned from a variety of materials into a various shapes. Examples of materials from which the housing may be made include plastics, metals, pressed or bonded fibrous composite structures. Depending on the materials used, and the desired structure of the resulting device, the housing may be made by various techniques, including injection molding, vacuum forming, die cutting, rapid prototyping, three dimensional computer aided manufacturing, stamping, die extrusion, and casting. The housing also could be a roll-based product—see for example, U.S. patent application Ser. No. 12/784,182 to Billingsley et al. The housing and the construction of the subsections may define the location of the filter layers relative to one another and to the overall structure.

The filter elements that are used in connection with the present invention may include one or more layers of particulate and/or gaseous filter media. Particulate filter media is fashioned to remove particulates that are suspended in the ambient air, and the gaseous media is fashioned to remove vapors that are suspended therein. The filtration layers may come in a variety of shapes and forms and for respirator use may have a thickness of about 0.2 millimeters (mm) to 2 centimeter (cm), or 0.5 to 1.5 cm, and it could be a generally planar filter or it could be corrugated to provide an expanded surface area—see, for example, U.S. Pat. Nos. 5,804,295 and 5,656,368 to Braun et al. Each filtration layer also may include multiple filtration layers joined together by an adhesive or any other means. The filter layers also may include parallel channels as described, for example, in U.S. Pat. Nos. 6,752,889 and 6,280,824 to Insley et al. The filtration media also may be a HEPA class filter. Essentially any suitable material that is known (or later developed) for forming a filtering layer may be used for the filtering material. Webs of melt-blown fibers, such as those taught in Wente, Van A., *Superfine Thermoplastic Fibers,* 48 Indus. Engn. Chem., 1342 et seq. (1956), especially when in a persistent electrically charged (electret) form are especially useful (see, for example, U.S. Pat. No. 4,215,682 to Kubik et al.). These melt-blown fibers may be microfibers that have an effective fiber diameter less than about 20 micrometers (μm) (referred to as BMF for blown microfiber). Effective fiber diameter may be determined according to Davies, C. N., *The Separation Of Airborne Dust Particles,* Institution Of Mechanical Engineers, London, Proceedings 1B, 1952. BMF webs that contain fibers formed from polypropylene, poly(4-methyl-1-pentene), and combinations thereof are commonly used. Electrically charged fibrillated-film fibers as taught in van Turnhout, U.S. Pat. Re. 31,285, also may be suitable, as well as rosin-wool fibrous webs and webs of glass fibers or solution-blown, or electrostatically sprayed fibers, especially in microfilm form. Electric charge can be imparted to the fibers by contacting the fibers with water as disclosed in U.S. Pat. No. 6,824,718 to Eitzman et al., U.S. Pat. No. 6,783,574 to Angadjivand et al., U.S. Pat. No. 6,743,464 to Insley et al., U.S. Pat. No. 6,454,986 and U.S. Pat. No. 6,406,657 to Eitzman et al., and U.S. Pat. No. 6,375,886 and U.S. Pat. No. 5,496,507 to Angadjivand et al. Electric charge also may be imparted to the fibers by corona charging as disclosed in U.S. Pat. No. 4,588,537 to Klasse et al. or by tribocharging as disclosed in U.S. Pat. No. 4,798,850 to Brown. Also, additives can be included in the fibers to enhance the filtration performance of webs produced through the hydro-charging process (see U.S. Pat. No. 5,908,598 to Rousseau et al.). Fluorine atoms, in particular, can be disposed at the surface of the fibers in the filter layer to improve filtration performance in an oily mist environment—see U.S. Pat. Nos. 6,398,847 B1, 6,397,458 B1, and 6,409,806 B1 to Jones et al. Typical basis weights for electret BMF filtration layers are about 10 to 100 grams per square meter. Packed beds of active-particulate also may be used as well as permeable shaped structures of active-particulate which are held together with, for example, PSA microparticulate—see U.S. Pat. No. 6,391,429 to Senkus et al.—or bonded sorbent particulate as described in U.S. Pat. No. 5,033,465 to Braun et al. An example of a fibrous matrix that contains active particulate is shown in U.S. Patent Application No. 2005/0169820A1. The sorbent particles may be enmeshed in the web, typically, such that there is at least about 60 weight percent sorbent particles enmeshed in the web. The fibers used in the particle-containing web typically have sufficiently greater crystallization shrinkage than similar fibers. The fibers typically comprise polypropylene, and the sorbent particles are typically evenly distributed in the web so that the web has an Adsorption Factor A of at least $1.6 \times 10^4$/millimeters (mm) water. The porous sheet articles typically exhibit a low pressure drop, have a long service life, and have an Adsorption Factor A exceeding that of packed-bed carbon. The Adsorption Factor A can be calculated using parameters or measurements similar to those described in Wood, JOURNAL OF THE AMERICAN INDUSTRIAL HYGIENE ASSOCIATION, 55(1):11-15 (1994). Further information regarding Adsorption Factor A may be found in the patent application cited above in this paragraph. The active-particulate that may be used in the filters of the present invention include particles or granules that are suited to perform some action or function attributable to some characteristic or property, including chemical change properties such as reaction, catalysis, and ion exchange, and/or physical properties such as high surface area, porosity, and relatively small size and shape. One example of active-particulate is particles that interact with components in a fluid to remove or alter their composition. The components in the fluid may be sorbed onto or into the active-particulate, or they may be reacted to make their composition more benign. The active-particulate accordingly may be sorptive, catalytic, or reactive. Examples of active-particulate materials that may be used in connection with the present invention include sorbent microparticulate granules, such as active carbon, chemically surface-treated activated carbon, alumina, silica gel, bentonite, kaolin diatomaceous earth, powdered zeolites (both natural and synthetic), ion exchange resins and molecular sieves, and particulates such as catalytic particles and particles containing encapsulated compounds. Commonplace active-particulates include activated carbon, chemically-treated carbon, and alumina particulate. Examples of commercially available activated carbon that may be used in the present invention include Kuraray 12×20 type GG (available from Kuraray Chemical Corporation, Osaka, Japan and Calgon 12×30 URC available from Calgon Carbon Corporation, Pittsburgh, Pa. Patents that describe various types of active-particulate that may be used in the present invention include U.S. Pat. No. 7,309,513 to Brey et al., U.S. Pat. No. 7,004,990 and U.S. Pat. No. 6,391,429 to Senkus et al., U.S. Pat. No. 6,767,860 to Hem et al., U.S. Pat. No. 5,763,078 to Braun et al., and U.S. Pat. No. 5,496,785 to Abler.

Although the invention has been described and illustrated for use in conjunction with personal respiratory protection devices like welding helmets and PAPRs, the invention also could be used with collective protection system or installations like buildings and tents. In such instances a plurality of tuned filtering devices—or stacks of such devices—could be used to filter air before it enters the building or installation; see, for example, U.S. Pat. No. 7,995,570 to Insley et al.

EXAMPLE

Air Flow Test

To verify that the air flow velocities through the subsections of a filter are substantially equal, differential air pressure between the filter subsections and ambient air pressure is measured. If ambient air pressure is not used, the baseline or reference pressure must measure the air velocity of all of the filter air flow and not a subset of the subsections. The pressure measurements can be done without filter media in the subsections or with the filter media in the subsections. If the filter media is located in the subsections during the measurements, the filter media used must be essentially the same in each of the subsections pertinent to the invention. The pressure measurement ports for the subsections that are not being measured must be plugged. The difference between the baseline value and each subsection is recorded.

Air Filter Construction

Figure 8:
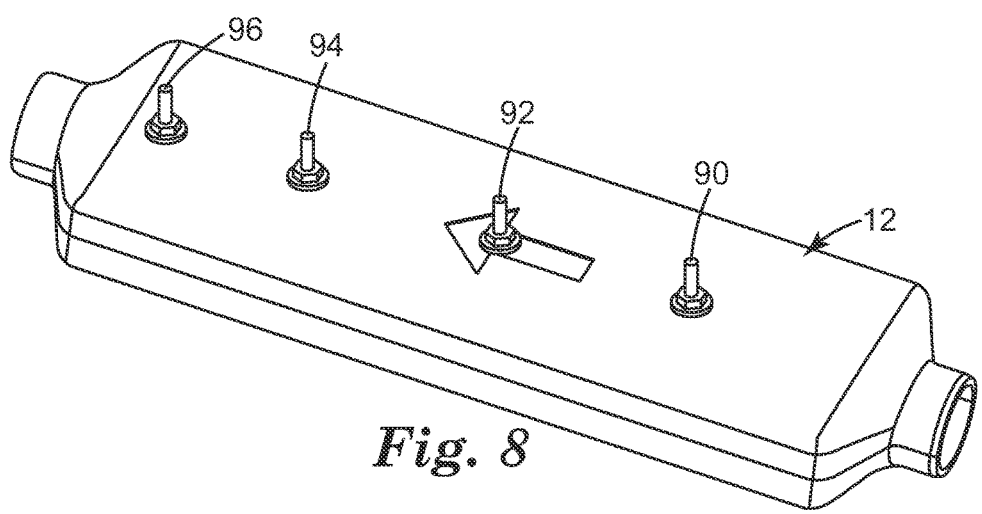
FIG. 8 is a perspective view of a filtering device 10' having ports 90-96 located thereon for measuring pressure in the various subsections of the filtering 10'.

A filter housing was designed and built, which contained six filter elements that were located in three subsections similar to the filtering device shown and described with reference to FIGS. 5-6. The air distribution systems for each of three subsections were designed so that each subsection would have equal air flow leading to it and away from it. Pressure measurement ports 90, 92, and 94 were located in each of the three subsections, respectively, as well as at a port 96 located at the outlet plenum of the filter as shown in FIG. 8. Port 96 measured the baseline pressure. The filter elements used in each subsection contained particulate filtering media and carbon loaded web to filter gaseous contaminants. The filter media used is described in U.S. Patent Application 2005/0169820 A1 to Tatarchuk et al. This filter media exhibited a measureable air flow resistance and contained active particulate entrapped within a matrix of microfibers.

Twenty-five liters per minutes of air were passed through the filter housing 12. An Extech 755 handheld device was used to measure the pressure difference between the Outlet 96 and each of the subsections 90-94 according to the Air Flow Test. The pressure measurements between the three sections are set forth below in Table 1:

TABLE 1

| Ports Measured | Pressure Difference (Pa) | Volume Flow (lpm) |
|---|---|---|
| 90 and 96 | 4.8 | 25 |
| 92 and 96 | 4.8 | 25 |
| 94 and 96 | 4.8 | 25 |

The data in Table 1 show that the pressure measured in each filtering subsection is similar the other subsections. The relative airflow velocity through each of the three subsections in the filtering device therefore is substantially the same. Having similar airflow velocities, the filtering device would be expected to exhibit benefits of extended service.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. An air filtering device that comprises:
   (a) a housing extending from a first location to a second location along a longitudinal dimension, wherein the housing includes three or more subsections disposed in series, each subsection containing a filter element;
   (b) an inlet disposed at the first location on the housing;
   (c) an upstream air distribution system in fluid communication with the inlet, wherein the upstream air distribution system defines a separate port for each of the three or more subsections and a plenum in upstream fluid communication with each of the subsections through the corresponding separate port, wherein each of the separate ports is positioned between the first location and all of the three or more subsections along the longitudinal dimension and each of the separate ports is adjacent the plenum such that air is configured to pass from the plenum and through the separate ports;
   (d) a downstream air distribution system located in fluid communication with each subsection; and
   (e) an outlet in fluid communication with the downstream air distribution system;
   wherein the upstream air distribution system, the three or more subsections, and downstream air distribution system are configured such that air entering the inlet passes in different directions toward each of the three or more subsections and flows through only one subsection between the inlet and the outlet.

2. The air filtering device of claim 1, wherein the subsections exhibit substantially the same airflow velocity.

3. The air filtering device of claim 1, wherein one or more of the subsections include a split flow filter.

4. The filtering device of claim 3, wherein the device is a filter cartridge that is adapted for use in a personal respiratory protection device.

5. A personal respiratory protection device that contains the filter cartridge of claim 4.

6. The personal respiratory protection device of claim 5 comprising a helmet, the filtering cartridge being located in the crown space of the helmet.

7. A powered air purifying respirator, which comprises the filter cartridge of claim 6 in the crown space of a helmet.

8. The filtering device of claim 1 wherein the upstream air distribution system contains the plenum and a manifold and the downstream air distribution system contains a plenum and a manifold.

9. The filtering device of claim 8, wherein the plenums, manifolds, and filter elements cause substantially the same airflow velocity through each subsection.

10. The filtering device of claim 1, wherein the air is delivered to each subsection through the plenum of the upstream air distribution system and one or more channels or passageways.

11. The filtering device of claim 10, wherein the air leaving each subsection travels through one or more channels or passageways.

12. The filtering device of claim 1, wherein the air entering a subsection is split into two airstreams.

13. The filtering device of claim 12, wherein the split flow airstream passes through opposing filter elements before exiting the subsection.

14. The filtering device of claim 1, wherein the airflow velocity in each subsection is within 5% of other subsections from a baseline value.

15. The filtering device of claim 1, wherein the subsections each contain particulate and/or gaseous filters.

16. The filtering device of claim 1, wherein each subsection contains a particulate filter element that contains microfibers, and wherein each subsection contains a gaseous filter element that contains active particulate.

17. The filtering device of claim 16, wherein each subsection contains one or more filter elements that are tilted relative to the airflow entering the subsection.

18. The filtering device of claim 1, wherein the device comprises 3 to 20 subsections.

19. The filtering device of claim 1, wherein the device contains 3 to 10 subsections.

20. An air filtering device that comprises:
   (a) a housing extending from a first location to a second location along a longitudinal dimension, wherein the housing contains 3 to 10 subsections disposed in series, each subsection containing a filter element, at least one of the subsections containing two or more filter elements;
   (b) an inlet disposed at the first location on the housing;
   (c) an upstream air distribution system in fluid communication with the inlet, wherein the upstream air distribution system defines a separate port for each of the 3 to 10 subsections and a plenum in upstream fluid communication with each of the subsections through the corresponding separate port, wherein each of the separate ports is positioned between the first location and all of the 3 to 10 subsections along the longitudinal dimension and each of the separate ports is adjacent the plenum such that air is configured to pass from the plenum and through the separate ports;
   (d) a downstream air distribution system located in fluid communication with each subsection; and
   (e) an outlet in fluid communication with the downstream air distribution system;
   wherein the upstream air distribution system, subsections, and downstream air distribution system are configured such that air entering the inlet passes in different directions toward each of the plurality of subsections and flows through only one subsection between the inlet and the outlet, and wherein the air entering the at least one of the subsections containing two or more filter elements is split into two airstreams such that the split flow airstream passes through opposing filter elements before exiting the subsection.

* * * * *